US00PP08606P

United States Patent [19]

VandenBerg

[11] Patent Number: Plant 8,606

[45] Date of Patent: Feb. 22, 1994

[54] CHRYSANTHEMUM PLANT NAMED REGAL DESIREE

[75] Inventor: Cornelis P. VandenBerg, Salinas, Calif.

[73] Assignee: Yoder Brothers, Inc., Barberton, Ohio

[21] Appl. No.: 826,067

[22] Filed: Jan. 27, 1992

[51] Int. Cl.[5] ..... A01H 5/00

[52] U.S. Cl. ..... Plt./74.1

[58] Field of Search ..... Plt. 74.1, 82.4

[56] References Cited

U.S. PATENT DOCUMENTS

Plt. 7500 4/1991 VandenBerg .....Plt./74.1

4,616,099 10/1986 Sparkes ..... 47/58

OTHER PUBLICATIONS

Broertjes, et al. 1980, "A mutant of a mutant of a . . . Irradiation of progressive radiation-induced mutants in a mutation breeding programme with *Chrysanthemum morifolium*", Euphytica 29:526–530.

Gosling, ed., 1979, "The Chrysanthemum Manual-6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of Chrysanthemums", Euphytica, 15:156–162.

Dowrick et al. 1966, "The induction of mutations in Chrysanthemum using X- and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Regal Desiree particularly characterized by its flat capitulum form; daisy capitulum type; dark purple ray floret color; diameter across face of capitulum of 25 to 29 mm when fully opened, when grown as a pinched spray pot mum; photoperiodic flowering response to short days of 42 to 47 days; plant height with 14 to 15 long days after sticking unrooted cuttings, and with 0 to 1 applications of 2500 ppm B-9 SP, ranges from 18 to 23 cm when grown as a pinched pot mum with 4 cuttings in a 15 cm pot; small dark green foliage; branching pattern is spreading and very prolific, each plant having 6 to 8 laterals after pinch; very floriferous, with an excellent display of many small flowers; and excellent tolerance to high temperatures for bud initiation and flower development.

1 Drawing Sheet

The present invention relates to a new and distinct cultivar of *Chrysanthemum, botanically known as Dendranthema grandiflora*, and referred to by the cultivar name Regal Desiree.

Regal Desiree, identified as 4124 (86-666C13), is a product of a mutation induction program. The new cultivar was discovered and selected by Cornelis P. VandenBerg on Jan. 30, 1990 in a controlled environment in Salinas, Calif., as one flowering plant within a flowering block established as rooted cuttings from stock plants which has been exposed as unrooted cuttings to an X-ray source of 1750 rads in Fort Myers, Fla., on Jul. 13, 1989. The irradiated parent cultivar was the cultivar identified as Desiree, disclosed in U.S. Plant Pat. No. 7,500, and described as a daisy spray pot mum with a flat capitulum form; a light purple ray floret color with the underside of the ray florets and the flower buds both being dark purple; diameter across face of capitulum of 30 to 32 mm when fully opened; flowering response period of 42 to 46 days after start of short days; plant height of 18 to 23 cm with 1 to 2 applications of 2500 ppm B-9 SP when grown as a pinched pot mum in a 15 cm pot; small dark green foliage; spreading and very prolific branching pattern, with 6 to 8 laterals after pinch; very floriferous, with an excellent display of many small flowers; and excellent tolerance to high temperatures for bud initiation and flower development.

The irradiation program resulting in Regal Desiree has as its primary objective the expansion of color ranges of the parent cultivar Desiree. The irradiation program comprises irradiating cuttings of the parent cultivar at irradation levels of 1500, 1750 and 2000 rads. A total of 1407 cuttings harvested from a total of 225 irradiated plants were planted on Nov. 6, Oct. 23 and Oct. 2, 1989. Of these, 25 initial selections were made, which selections were then revegetated and reflowered. Three consecutive flowerings resulted in discarding 23 of the original 25 selections on Oct. 26, 1990. Two selections were retained. One of these selections, referred to as Light Bronze Desiree, was discarded on Nov. 20, 1991, and the one remaining selection will be introduced as Regal Desiree.

The first act of asexual reproduction of Regal Desiree was accomplished when vegetative cuttings were taken from the initial selection in Apr. 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Regal Desiree are firmly fixed and are retained through successive generations of asexual reproduction.

Regal Desiree has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Regal Desiree, which, in combination, distinguish this Chrysanthemum as a new and distinct cultivar:

1. Flat capitulum form.
2. Daisy capitulum type.
3. Dark purple ray floret color.
4. Diameter across face of capitulum of 25 to 29 mm when fully opened, when grown as a pinched spray pot mum.
5. Photoperiodic flowering response to short days of 42 to 47 days.
6. Plant height, with 14 to 15 long days after sticking unrooted cuttings, and with 0 to 1 applications of 250 ppm B-9 SP, ranges from 18 to 23 cm when grown as a pinched pot mum with 4 cuttings in a 15 cm pot.
7. Small dark green foliage.
8. Branching pattern is spreading and very prolific, each plant having 6 to 8 laterals after pinch.
9. Very floriferous, with an excellent display of many small flowers.
10. Excellent tolerance to high temperatures for bud initiation and flower development.

The accompanying photographic drawing is a side view of a potted mum of Regal Desiree, with 4 cuttings in a 15 cm pot, with the colors being as nearly true as possible with illustrations of this type.

Of the commercial cultivars known to the inventor, the most similar in comparison to Regal Desiree is the parent Desiree. All traits of Regal Desiree are similar to those of Desiree, except for the ray floret color and the diameter of capitulum. The ray floret color of Regal Desiree is significantly darker than the ray floret color of Desiree. The diameter of capitulum of Regal Desiree is 3 to 5 mm smaller than the diameter of capitulum of Desiree.

In the following description color references are made to The Royal Horticultural Society Colour Chart. The color values were determined on plant material grown as a pinched spray pot mum in Salinas, Calif., on Jul. 22, 1991.

Classification:

*Botanical.*—*Dendranthema grandiflora* cv Regal Desiree.

*Commercial.*—Flat daisy spray pot mum.

INFLORESCENCE

A. Capitulum:

*Form.*—Flat.

*Type.*—Daisy.

*Diameter across face.*—25 to 29 mm when fully opened.

B. Corolla of ray florets:

*Color (general tonality from a distance of three meters).*—Dark purple.

*Color (upper surface).*—Color is between 61A and 71A.

*Color (under surface).*—Closest to 72A. The base of the ray florets is white on both upper and under side. This white portion of the ray floret is slightly visible on the under side, but is not visible on the upper side, being covered by the disc florets.

*Shape.*—Straight, oblong, slightly ribbed.

C. Corolla of disc florets:

*Color (mature).*—Closest to 12A.

*Color (immature).*—Closest to 1B.

D. Reproductive organs:

*Androecium.*—Present on disc florets only; scant pollen.

*Gynoecium.*—Present on both ray and disc florets.

PLANT

A. General Appearance:

*Height.*—18 to 23 cm when grown as a pinched pot mum with 14 to 15 long days after sticking unrooted cuttings, and with 0 to 1 applications of 2500 ppm B-9 SP.

*Branching pattern.*—Spreading and very prolific, each plant having 6 to 8 laterals after pinch.

B. Foliage:

*Color (under surface).*—147A.

*Color (under surface).*—147B.

*Shape.*—Small, lobed and slightly serrated.

I claim:

1. A new and distinct Chrysanthemum plant named Regal Desiree, as described and illustrated.

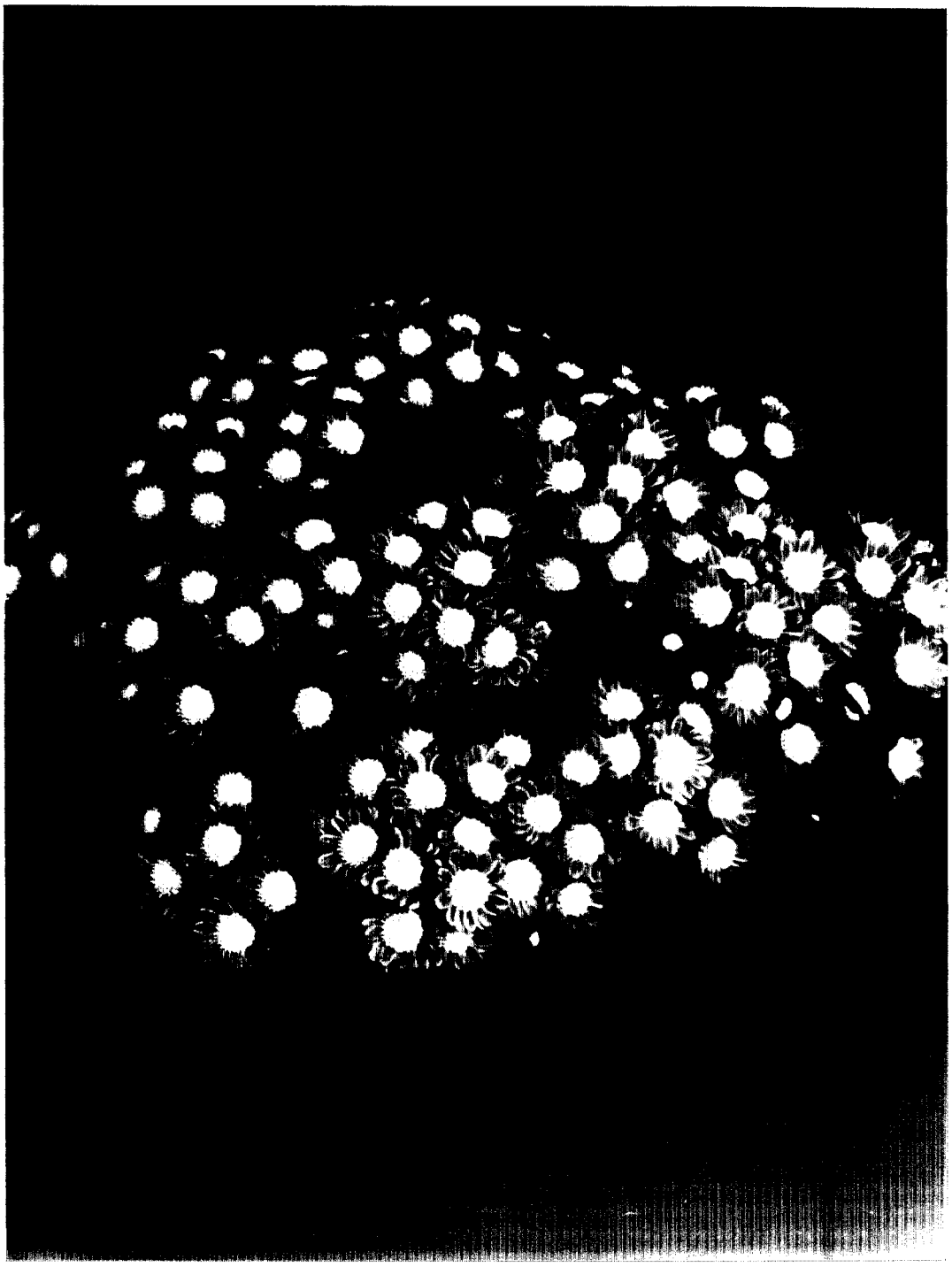

* * * * *